United States Patent [19]

Goldberg

[11] Patent Number: 5,102,887
[45] Date of Patent: Apr. 7, 1992

[54] METHOD FOR REDUCING EMESIS AND NAUSEA INDUCED BY THE ADMINISTRATION OF AN EMESIS CAUSING AGENT

[75] Inventor: Leon I. Goldberg, Chicago, Ill.

[73] Assignee: Arch Development Corporation, Chicago, Ill.

[21] Appl. No.: 540,884

[22] Filed: Jun. 15, 1990

Related U.S. Application Data

[63] Continuation of Ser. No. 312,117, Feb. 17, 1989, abandoned.

[51] Int. Cl.$^5$ .............................................. A61K 31/44
[52] U.S. Cl. ................................................... 514/282
[58] Field of Search ........................................ 514/282

[56] References Cited

U.S. PATENT DOCUMENTS 4,719,215 1/1988 Goldberg ........................... 514/282

OTHER PUBLICATIONS

Krueger et al, "The Pharmacology of the Opium Alkaloids," *Public Health Reports,* Supplement No. 165, Part I, p. 603 and Part II, p. 817 (1940).

Janssen et al, "Chemistry and Pharmacology of Compounds Related to 4-(4-hydroxy-4-phenyl-piperidino)-butyrophenone, Part II—Inhibition of Apomorphine Vomiting in Dogs," *Artzneim-Forsch,* vol. 9, pp. 765-767 (1959).

*Primary Examiner*—S. J. Friedman
*Attorney, Agent, or Firm*—Christie, Parker & Hale

[57] ABSTRACT

A method for preventing or relieving nausea and emesis associated with the use of an emesis-causing agent in warm-blooded animals comprises administering to the animal both a narcotic analgesic and a quaternary derivative of noroxymorphone prior to, simultaneously with of after administering the emesis-causing agent. A particularly preferred noroxymorphone derivative is methylnaltrexone. The method is highly effective in preventing or relieving nausea and emesis induced by anti-cancer drugs, and by apomorphine.

10 Claims, No Drawings

METHOD FOR REDUCING EMESIS AND NAUSEA INDUCED BY THE ADMINISTRATION OF AN EMESIS CAUSING AGENT

This is a continuation of application Ser. No. 312,117 filed Feb. 17, 1990, now abandoned.

FIELD OF THE INVENTION

This invention relates to the treatment of nausea and vomiting resulting from the administration of emesis-causing agents to animals, and more particularly, to the administration of a combination of a quaternary derivative of noroxymorphone and a narcotic analgesic to prevent or at least reduce nausea and vomiting resulting from the administration of emesis-causing agents.

BACKGROUND OF THE INVENTION

Effective treatment of many illnesses involves the administration of one or more therapeutic drugs. Many therapeutic drugs, however, produce adverse side effects such as nausea and emesis. These side effects often limit the usefulness of the drug and may even render the drug unacceptable for use. For example, the administration of therapeutic doses of many anti-cancer drugs, e.g., cisplatin, is often accompanied by nausea and emesis. Many clinically useful narcotic analgesics such as morphine and related opiates, meperidine, methadone and the like, given to ease pain, also produce nausea and emesis. Apomorphine, a synthetic opiate obtained by treating morphine with hydrochloric acid, is another example of an emetic agent.

U.S. Pat. No. 4,719,215 to Goldberg, incorporated herein by reference, discloses that quaternary derivatives of noroxymorphone, such as methylnaltrexone, are useful for the treatment, both prophylactic and therapeutic, of the nausea and vomiting associated with the administration of narcotic analgesics such as morphine and the like without interfering with the analgesic activity of the drug.

Methylnaltrexone and other quaternary derivatives of noroxymorphone have proven ineffective at relieving nausea and emesis caused by the administration of other emesis-causing agents such as anticancer drugs, apomorphine and the like.

SUMMARY OF THE INVENTION

It has now been discovered that nausea and emesis resulting from the administration of emesis-causing agents other than narcotic analgesics may be prevented or at least reduced by also administering the combination of a quaternary derivative of noroxymorphone and a narcotic analgesic. The quaternary derivative of noroxymorphone is represented by the formula:

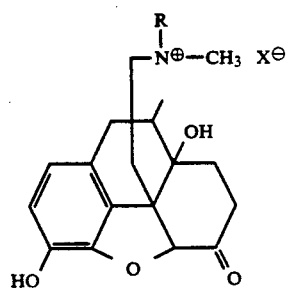

wherein R is allyl or a related radical such as chlorallyl, cyclopropyl-methyl or propargyl, and X is the anion of an acid, especially a chloride, bromide, iodide or methylsulfate anion. The presently preferred quaternary derivative of noroxymorphone is methylnaltrexone. The narcotic analgesic may be any narcotic agonist which acts on morphine receptors. Morphine salts, e.g., morphine sulfate, are presently preferred.

The quaternary derivative of noroxymorphone may be administered prior to, simultaneously with, or following the administration of the narcotic analgesic. Both the quaternary derivative of noroxymorphone and the narcotic analgesic are preferably administered prior to administration of the emesis-causing agent.

Preferably, the quaternary derivative of noroxymorphone is administered in a dosage of from about 0.05 mg/kg to about 1.0 mg/kg of animal body weight. The preferred dosage level of narcotic analgesic is up to about 2.0 mg/kg of animal body weight.

DETAILED DESCRIPTION

This invention relates to the use of the combination of a narcotic analgesic and a quaternary derivative of noroxymorphone to prevent or at least reduce nausea and emesis associated with the administration of an emesis-causing agent to warm-blooded animals. Example of emesis-causing agents to what the invention is believed applicable include drugs such as cisplatin, cyclophosphamide, anthracyclines, nitroureas, DTIC, methotrexate, 5-fluorouracil, dipamine and emetine, a drug used to treat amebeases.

Quaternary derivatives of noroxymorphone are compounds represented by the formula:

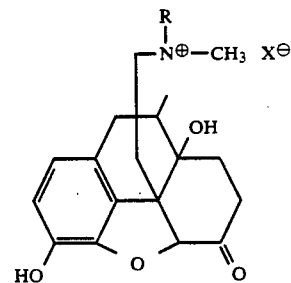

wherein R is allyl or a related radical such as chlorallyl, cyclopropyl-methyl or propargyl, and X is the anion of an acid, especially a chloride, bromide, iodide, or methylsulfate anion The compounds are synthesized as described in U.S. Pat. No. 4,176,186, the disclosure of which is incorporated herein by reference A particularly preferred noroxymorphone derivative is methylnaltrexone, but other compounds represented by the above formula are also suitable.

As used therein, "narcotic analgesics" refers to narcotic agonists which act on morphine receptors. Narcotic agonists include morphine and related opiates, meperidine, methadone and the like and salts thereof, as is well-known in the art. Salts of morphine, e.g. morphine sulfate, are presently preferred.

The narcotic analgesic and the noroxymorphone derivative may be administered to the patient either separately or together. The method of administration may be either enteral or parenteral. A preferred method of administration is by separate injection wherein the patient is given an injection of noroxymorphone derivative followed. The narcotic analgenic is preferably within about two hours of the noroxymorphone derivative by an injection of narcotic analgesic is then followed preferably within about 30 to 45 minutes by the administration of the emesis-causing agent. It is understood that, if desired, the noroxymorphone derivative may be administered concurrently with or even following the administration of the narcotic analgesic, if the particular narcotic analgesic does not produce immediate vomiting. If following, it is preferred that the noroxymorphone derivative be administered within a few minutes of the narcotic analgesic. Likewise,.while not preferred, it is understood that the emesis-causing agent may be administered concurrently with or, if it does not induce immediate vomiting, prior to administering the noroxymorphone derivative and narcotic analgesic, if desired. If prior, it is apparent that the noroxymorphone derivative and narcotic analgesic be administered before the onset of emesis.

The noroxymorphone derivative is preferably administered in the range of from about 0.05 mg/kg to about 1.0 mg/kg of animal body weight. The narcotic analgesic is preferably administered in a positive amount of up to about 2.0 mg/kg and more preferably, a positive amount of up to about 1.0 mg/kg of animal body weight.

The effect of methylnaltrexone and a morphine-based narcotic analgesic in reversing the emetic effects of cisplatin, a chemotherapeutic agent, and apomorphine, a well-known emetic is illustrated herein. Both of these drugs produce emesis by a mechanism different from that of morphine and other narcotic agonists The unit of mg/kg refers to milligrams of substance administered per kilograms of animal body weight.

CONTROL 1 AND EXAMPLE 1

0.25 mg/kg of methylnaltrexone was administered intravenously to five dogs. Thirty minutes later, 3 mg/kg of cisplatin was administered intravenously to each dog. All five dogs vomited. The onset of emesis averaged two hours, fifty minutes and fifty-one seconds. The animals experienced an average of 11.6 episodes of emesis. Methylnaltrexone, alone, was not effective in blocking the emesis induced by cisplatin.

Five separate dogs were then given 0.25 mg/kg of methylnaltrexone intravenously and 1 mg/kg of morphine intravenously. None of the dogs vomited. Thirty minutes later, 3 mg/kg of cisplatin was administered intravenously to each dog. No vomiting was observed during an initial ninety minute observation period. After ninety minutes. 0.25 mg/kg of methylnaltrexone and 0.5 mg/kg of morphine were administered intravenously to each dog. No vomiting was observed during a five hour observation period. The dogs' cages were checked on the morning following the studies; no vomit was found in the cages. The combination of methylnaltrexone and morphine was 100% effective in preventing cisplatin-induced emesis.

CONTROL 2 AND EXAMPLE 2

0.03 mg/kg of apomorphine was administered intravenously to seven dogs. All seven vomited. The average onset of emesis was two minutes and twenty seconds, with an average of 3.57 episodes of emesis. The administration of apomorphine uniformly induced emesis.

0.25 mg/kg of methylnaltrexone was administered intravenously to four dogs. Thirty minutes later 0.03 mg/kg of apomorphine was administered intravenously to each dog. All four dogs vomited. The onset of emesis averaged one minute and sixteen seconds. Two animals had three episodes of emesis, and two animals had four episodes. Methylnaltrexone, alone, was not effective in blocking the emesis induced by apomorphine.

Nine dogs were each given 0.25 mg/kg methylnaltrexone intravenously, and fifteen minutes later each was given 1 mg/kg of morphine sulfate intravenously. Thirty minutes later 0.03 mg/kg of apomorphine was administered intravenously to each dog. Two dogs vomited. The onset of emesis was one minute and forty seconds in one animal, and three minutes and twenty-nine seconds in the other animal. One of the two dogs vomited three times, and the other dog vomited once. Seven of the dogs experienced no vomiting. The combination of methylnaltrexone and morphine sulfate was about 78% effective in preventing emesis produced by a dose of apomorphine which causes 100% emesis in the absence of the combination.

The invention has been described above in detail with respect to specific emesis-causing agents. It is understood that the invention is equally applicable to other emesis-causing agents. Accordingly, the foregoing description should not be read as pertaining only to the specific emesis-causing agents described, but rather should be read consistent with and as support for the following claims which are to have their fullest fair scope.

What is claimed is:

1. A method for preventing or relieving nausea and emesis associated with the use of emesis-causing agents in warm-blooded animals, which comprises administering to an animal an effective amount of a narcotic analgesic and a quaternary derivative of noroxymorphone having compound of the formula:

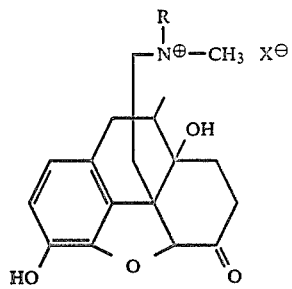

wherein R is allyl or a related radical such as chlorallyl, cyclopropyl-methyl or propargyl, and x is the anion of an acid, especially a chloride, bromide, iodide or methylsulfate anion, prior to, simultaneous with or after administering an emesis-causing agent different from the narcotic analgesic.

2. A method as claimed in claim 1, where the narcotic analgesic is selected from the group consisting of morphine, morphine hydrobromide, morphine hydrochloride, and morphine sulfate.

3. A method as claimed in claim 1, where the quaternary derivative of noroxymorphone is administered to the animal in an amount between about 0.05 mg/kg and about 1.0 mg/kg of animal body weight.

4. A method as claimed in claim 1, where the narcotic analgesic is administered to the animal in an amount of up to about 2.0 mg/kg of animal body weight.

5. A method as claimed in claim 1, where the quaternary derivative of noroxymorphone is methylnaltrexone.

6. A method as claimed in claim 1, wherein the narcotic analgesic quaternary derivative of noroxymorphone are administered to the animal prior to the administration of the emesis-causing agent.

7. A method as claimed in claim 1, where the quaternary derivative of noroxymorphone is administered to the animal prior to the administration of the narcotic analgesic.

8. A method for preventing or relieving nausea and emesis associated with the use of an emesis-causing agent in warm-blooded animals, which comprises administering to an animal the combination of methylnaltrexone in any amount of from about 0.05 to about 1.0 mg/kg and a narcotic analgesic selected from the group of morphine, morphine, hybromide, morphine hydrochloride, morphine sulfate and mixtures thereof, in an amount of up to about 2 mg/kg prior to, simultaneously with or after administering an emesis-causing agent different from the narcotic analgesic.

9. A method as claimed in claim 8, wherein the methylnaltrexone and narcotic analgesic are administered to the animal prior to administering the emesis-causing agent.

10. A method as claimed in claim 9, wherein the methylnaltrexone is administered to the animal prior to administering the narcotic analgesic.

* * * * *

UNITED STATES PATENT AND TRADEMARK OFFICE
CERTIFICATE OF CORRECTION

PATENT NO. : 5,102,887

DATED : April 7, 1992

INVENTOR(S) : Leon I. Goldberg

It is certified that error appears in the above-identified patent and that said Letters Patent is hereby corrected as shown below:

On the Title Page:

Abstract, line 6, before "after" change "of" to -- or --.

Column 2, line 51, after "anion" insert a period.
Column 2, line 54, after "reference" insert a period.

Column 3, line 2, delete "followed".
Column 3, line 2, change "analgenic" to -- analgesic --.
Column 3, line 4, change "norexymorphone" to -- noroxymorphone --.
Column 3, line 34, after "agonists" insert a period.

Column 4, line 55, change "x" to -- X --.

Column 6, line 4, after "morphine" (second occurrence) delete the comma.

UNITED STATES PATENT AND TRADEMARK OFFICE
CERTIFICATE OF CORRECTION

PATENT NO. : 5,102,887

DATED : April 7, 1992

INVENTOR(S) : Leon I. Goldberg

It is certified that error appears in the above-identified patent and that said Letters Patent is hereby corrected as shown below:

Column 6, line 4, after "morphine" (second occurrence) delete the comma.

Signed and Sealed this

Tenth Day of August, 1993

Attest:

MICHAEL K. KIRK

*Attesting Officer*   Acting Commissioner of Patents and Trademarks